(12) United States Patent
Ceresa et al.

(10) Patent No.: US 9,320,691 B2
(45) Date of Patent: Apr. 26, 2016

(54) STABLE COMPOSITIONS AND METHODS FOR PREPARING THE SAME

(75) Inventors: Alan Carlo Ceresa, Allschwil (CH); René Heckendorn, Basel (CH); Madeleine Manns, Riehen (CH)

(73) Assignee: GABA International Holdings AG (CH)

( * ) Notice: Subject to any disclaimer, the term of this patent is extended or adjusted under 35 U.S.C. 154(b) by 242 days.

(21) Appl. No.: 14/343,698

(22) PCT Filed: Sep. 9, 2011

(86) PCT No.: PCT/EP2011/065681
§ 371 (c)(1),
(2), (4) Date: Mar. 7, 2014

(87) PCT Pub. No.: WO2013/034196
PCT Pub. Date: Mar. 14, 2013

(65) Prior Publication Data
US 2014/0205549 A1    Jul. 24, 2014

(51) Int. Cl.
*A61K 8/19* (2006.01)
*A61Q 11/00* (2006.01)
*A61K 8/36* (2006.01)
*G01N 27/416* (2006.01)
*C07F 7/00* (2006.01)

(52) U.S. Cl.
CPC ... *A61K 8/19* (2013.01); *A61K 8/36* (2013.01); *A61Q 11/00* (2013.01); *C07F 7/003* (2013.01); *G01N 27/4161* (2013.01); *A61K 2800/522* (2013.01)

(58) Field of Classification Search
USPC ............................ 148/23; 424/49, 52; 525/528
See application file for complete search history.

(56) References Cited

U.S. PATENT DOCUMENTS

| 2,895,862 | A | * | 7/1959 | Laudenslager, Jr. | ............ 148/23 |
| 3,983,227 | A | | 9/1976 | Tofe et al. | |
| 4,269,958 | A | | 5/1981 | Gaylord | |
| 4,427,647 | A | | 1/1984 | Brockas et al. | |
| 5,073,485 | A | | 12/1991 | Amano et al. | |
| 5,258,173 | A | | 11/1993 | Waterfield | |
| 5,693,314 | A | * | 12/1997 | Campbell et al. | ................ 424/49 |
| 5,780,015 | A | * | 7/1998 | Fisher et al. | .................... 424/52 |
| 6,464,963 | B1 | | 10/2002 | Gambogi et al. | |
| 2006/0211831 | A1 | * | 9/2006 | Nishiguchi et al. | ........... 525/528 |
| 2009/0136432 | A1 | | 5/2009 | Strand et al. | |
| 2011/0020246 | A1 | | 1/2011 | Strand | |
| 2011/0020248 | A1 | * | 1/2011 | Strand | ............................. 424/52 |
| 2011/0027196 | A1 | | 2/2011 | Sharma | |
| 2013/0039867 | A1 | | 2/2013 | Heckendorn et al. | |

FOREIGN PATENT DOCUMENTS

| CN | 101579624 | 11/2009 |
| EP | 2281543 | 2/2011 |
| EP | 2281544 | 2/2011 |
| FR | 1488334 | 7/1967 |
| WO | WO 96/19183 | 6/1996 |
| WO | WO 02/15809 | 2/2002 |
| WO | WO 2009/130319 | 10/2009 |

OTHER PUBLICATIONS

Donaldson et al., 1961, "Basic Tin(II) Nitrate," J. Chem. Soc. 1996-2000.
Farrow et al., 1970, "The Nitrate Detinning Reaction in Model Systems," J. Food Sci. 35:818-822.
Hamdan, 2010, "SN (II) Selective 2-Amino-1,4-Naphthoquinone Derived Poly (Vinyl Chloride) Membrane Sensors," International J. Electrochem. Sci. 5:215-231.
International Search Report and Written Opinion in International Application No. PCT/EP2011/065681, mailed Nov. 12, 2012.
National Academy of Sciences, 1952, Literature of Dental Caries, pp. 402-404.
Robertson, 2006, "Nitrates in Detinning Process," Food Packaging, p. 151.
Hefferren, J.J.: "Laboratory analysis of toothpastes containg anticaries agents", Journal of the Society of Cosmetic Chemists, vol. 18, Feb. 5, 1967, pp. 135-140.

\* cited by examiner

*Primary Examiner* — Walter Webb

(57) ABSTRACT

Described herein are stable aqueous stannous ion containing compositions and methods of preparing and using the same.

20 Claims, No Drawings

STABLE COMPOSITIONS AND METHODS FOR PREPARING THE SAME

BACKGROUND

Stannous ions (divalent) are susceptible to oxidation by atmospheric oxygen, particularly in the mainly aqueous media found in these compositions. The oxidation gives stannic ions (tetravalent) which extensively hydrolyze in the aqueous medium to form insoluble hydroxo or oxide species which lead to precipitates and turbidity. This is unwanted e.g. for any quantitative stannous ion analytics of oral care formulations, which accordingly must be done with exclusion of atmospheric oxygen to prevent loss of soluble, quantifiable stannous ions as precipitated, not easily quantifiable, stannic ions.

SUMMARY

Some embodiments of the present invention provide a stable aqueous stannous ion containing composition comprising a liquid phase comprising dissolved tin in the formal oxidation state +II, one or more dissolved nitrates and a dissolved carboxylic acid which is non-chelating for the dissolved tin in the formal oxidation state +II, the liquid aqueous phase having a pH value of 2 to 4.

Other embodiments provide the use of one or more nitrates and a carboxylic acid which is non-chelating for tin in the formal oxidation state +II, for improving the stability of tin in the formal oxidation state +II against oxidation by molecular oxygen, wherein said one or more nitrates, carboxylic acid and tin in the formal oxidation state +II are dissolved in a liquid aqueous phase having a pH of 2 to 4.

Still further embodiments provide a process for improving the stability of tin in the formal oxidation state +II being dissolved in a liquid aqueous phase against oxidation by molecular oxygen, comprising dissolving in the liquid phase one or more nitrate salts and a carboxylic acid which is non-chelating for tin in the formal oxidation state +II, and adjusting the pH of the liquid aqueous phase to 2 to 4.

While other embodiments provide a process for the quantitative determination of tin in the formal oxidation state +II being dissolved in a liquid aqueous phase, wherein said tin in the formal oxidation state +II is determined by a quantitative oxidation to stannic ions, wherein the liquid aqueous phase comprises one or more dissolved nitrates.

In some embodiments, the present invention provides a process for the preparation of an oral care formulation, comprising mixing a stable aqueous stannous ion containing composition comprising a liquid aqueous phase with a customary oral care formulation ingredient or excipient.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls. Unless otherwise specified, all percentages and amounts expressed herein and elsewhere in the specification should be understood to refer to percentages by weight. The amounts given are based on the active weight of the material.

The term "liquid aqueous phase" preferably means for the purposes of the invention that the liquid phase is a liquid at room temperature. By "aqueous" is understood that the liquid phase contains typically 70 to 99 percent by weight water, as determinable by Karl-Fischer titration, whereby the upper limit of the water content may also be determined by the amounts of the other components found in the liquid phase.

In some embodiments, the liquid aqueous phase has a dynamic viscosity of not more than 1500 mPa·s at room temperature. In other embodiments, the liquid aqueous phase has a dynamic viscosity of 500 to 1500 mPa·s at room temperature. In some embodiments, the molecular oxygen is atmospheric oxygen solubilized in the liquid aqueous phase.

Surprisingly however it has now been observed that dissolved nitrates, in particular when used in combination with a dissolved carboxylic acid which is non-chelating for dissolved tin in the formal oxidation state +II and at a pH of 2 to 4, does not appreciably alter its oxidability by other pH-dependent (e.g. periodates, permanganates, persulfates, iron (III)chloride, percarboxylates such as perbenzoic acid and peracetic acid, peroxymonosulfate, peroxodisulfate) or pH-independent oxidants, wherein "pH-independent" is preferably understood as pH-independent in the pH range of 1 to 7, more preferably 2 to 6 (e.g. molecular halogens such as molecular chlorine, bromine or iodine, in particular molecular iodine; triiodide such as potassium triiodide; hexacyano-ferrates such as potassium hexacyanoferrate, or silver salts such as silver nitrate or silver perchlorate).

This means that quantitative determinations of dissolved tin in the formal oxidation state +II using a quantitative oxidation step to stannic ions in an aqueous phase containing nitrates are not adversely affected as such, but may be run without special precautions against atmospheric oxygen such as degassing and/or an inert gas atmosphere. The procedure for the quantitative determination of dissolved tin in the formal oxidation state +II, including the endpoint detection, in the presence of nitrates in the liquid aqueous phase may be analogous to the corresponding determination in a liquid aqueous phase devoid of nitrates. The endpoint detection may be by color, when the oxidant in its oxidized and reduced states has different colors. An example therefore is an oxidative determination using molecular iodine or triiodide as the oxidant; here the presence of excess oxidant may be shown by the blue color of the iodine complex with starch, whereas the reduced iodide anion is colorless. A further example of endpoint detection is an electrochemical detection, when the presence of excess oxidant not reduced anymore is visible by a potential rise on an electrode such as a platinum electrode. The quantitative determination of dissolved tin in the formal oxidation state +II may be a direct determination, i.e. wherein the dissolved tin in the formal oxidation state +II is directly titrated to the endpoint with the oxidant, or it may be indirect, i.e. first an excess of oxidant is added to oxidize all of the dissolved tin in the formal oxidation state +II to stannic ions, and then the excess oxidant is titrated back with another reducing agent, such as thiosulfate, to the endpoint.

As used herein, the term "dissolved tin in the formal oxidation state +II" is intended to encompass all ionic tin species in the formal oxidation state +II solubilized in the liquid aqueous phase. Examples of such tin species are hydrated stannous ions, soluble ionic or nonionic complexes of stannous ions and ionic hydroxo complexes of stannous ions. The source of the dissolved tin in the formal oxidation state +II is not critical and may be given by the sample which is to be analyzed. Solely by way of illustration stannous chloride, stannous fluoride, stannous hydroxide, and stannous sulfate are given as examples for the source.

In some embodiments, nitrates dissolved in the aqueous phase are used. The term "nitrates" encompasses all water-soluble inorganic species containing one or more $NO_3^-$ moieties each (coordinated to a cation or as counter anion(s)). Examples of nitrates are nitrato complexes of metal cations present in the aqueous phase, in particular of the stannous ions forming part of the dissolved tin in the formal oxidation state +II, solvated nitrate counter anions and undissociated nitric acid. The solvated nitrate anions are assumed to be nitrate anion solvated by water molecules and having essentially non-complexing cations, such as of sodium, potassium or the cations of amine fluorides cation (see below) as counter ions. Since all these nitrates will normally be in thermodynamic equilibrium with each other it is not possible to determine the molar amounts of each of these nitrates individually. The common feature of all these nitrates is, however, that upon alkalinization they are converted to solvated nitrate anions by deprotonation and/or by precipitation of the metal cations from any nitrato complexes as insoluble hydroxides or oxides. Said dissolved nitrates may be obtained by adding a salt of nitrate, preferably an alkali metal nitrate salt (e.g. lithium, sodium or potassium nitrate), an earth alkaline metal nitrate salt (e.g. magnesium or calcium nitrate), or an ammonium or tetraalkylammonium salt (e.g. ammonium, tetramethylammonium, tetraethylammonium or tetrabutylammonium nitrate) to the aqueous phase. More preferred is the addition of the nitrate as an alkali metal salt thereof, most preferably as sodium or potassium nitrate.

In some embodiments, a carboxylic acid which is non-chelating for dissolved tin in the formal oxidation state +II is optionally co-used. This is to be understood that the complex forming constant $K_{cb}$ $$K_{cb} = \frac{[ML_n]}{[M][L]^n}$$

of the acid's conjugate base for the dissolved tin in the formal oxidation state +II is at the most ten times the complex forming constant $K_a$ $$K_a = \frac{[MAc_2]}{[M][Ac]^2}$$

of acetate for dissolved tin in the formal oxidation state +II. This is synonymous to $\log(K_{cb}/K_a) \leq 1$.

In the above formulae for $K_{cb}$ and $K_a$ [M] is the concentration of not complexated dissolved tin in the formal oxidation state +II; [L] is the concentration of non-complexated conjugated base; [Ac] is the concentration of non-complexated acetate; [MAc$_2$] is the concentration of acetate-complexated dissolved tin in the formal oxidation state +II, and [ML$_n$] is the concentration of dissolved tin in the formal oxidation state +II complexated by the conjugate base in question (with n as the number of molecules of conjugate base).

The determination of such $K_{cb}$ and $K_a$ can be done electrochemically at room temperature in aqueous solution at a pH two units above the pKa value of the studied acid/conjugate base pair (e.g. at 6.75 for acetic acid/acetate pair, when $K_a$ is determined); by a) plotting values of $$\ln\left(\frac{[M_0] - [M]}{([L_0] - n([M_0] - [M]))^n}\right)$$

against values of ln([M]), obtained at a given, constant total concentration of conjugate base, [L$_0$], but at variable total concentrations of dissolved tin in the formal oxidation state +II, [M$_0$], the corresponding [M] being measured electrochemically with a stannous ion-selective electrode, such as the one described in Int. J. Electrochem. Sci. 5, pp. 215-231 (2010), b) linearly interpolating in the nernstian (linear) region the plotted value pairs, with a fixed slope of 1, and c) obtaining ln($K_{cb}$) or ln($K_a$) as the intersection of the obtained interpolating line with the y-axis of the plot.

These measurements may be done at concentrations low enough (typically not more than 0.2 M for either [L$_0$] and [M$_0$]) that the concentrations themselves, not the activities, can be used in the formulae.

Since the conjugate base is asked to be non-chelating for dissolved tin in the formal oxidation state +II by the above definition, then even more the carboxylic acid itself will be non-chelating for dissolved tin in the formal oxidation state +II.

In some embodiments the non-chelating carboxylic acid is preferably a monocarboxylic acid not substituted by any hydroxy groups and/or is selected from the group consisting of C1-C4 linear or branched alkanoic acids, C3-C5 linear, optionally alkyl-substituted alkenoic acids and C6-C14 aryl carboxylic acids. Preferred examples for monocarboxylic acids not substituted by any hydroxy groups are C1-C4 linear or branched alkanoic acids selected from the group consisting of formic acid, acetic acid, propionic acid and 2-methylpropionic acid; C3-C5 linear, optionally alkyl-substituted alkenoic acids selected from the group consisting of acrylic acid, methacrylic acid, tiglic acid and angelic acid; and C6-C14 aryl monocarboxylic acids selected from the group consisting of benzoic acid and 1- or 2-naphtalene carboxylic acid. More preferred examples for the monocarboxylic acid not substituted by any hydroxy groups are C1-C4 linear or branched alkanoic acids, and most preferred is acetic acid.

The carboxylic acid may, depending on the pH of the liquid aqueous phase, be in equlibrium with a certain amount of its conjugate base. It is, however, for the purposes of the invention not necessary that the conjugate base be present in such an amount as to form together with the free acid an actual buffer system.

As used herein, "conjugate base of the acid" refers to the chemical species obtainable from the carboxylic acid in question by removal of the carboxyl proton; or, in the case of fully protonated polycarboxylic acids, the chemical species obtainable by removal of the first (most acidic) carboxyl proton, or, in the case of polycarboxylic acids already partially deprotonated at their carboxyl groups, the chemical species obtainable by removal of one further carboxyl proton.

The carboxylic acid is required for the purposes of the invention to be dissolved in the aqueous phase. This implies that the carboxylic acid preferably has a solubility in water of at least about 0.1 g/100 ml water at room temperature.

In some embodiments the pH of the overall liquid aqueous phase is required to be in the range of 2 to 4 with co-use of a non-chelating carboxylic acid. In some embodiments, the pH of the liquid aqueous phase is in the range of 2.5 to 3.5 and even more preferably in the range of 2.7 to 3.3. In other embodiments without co-use of the non-chelating carboxylic acid, the pH of the liquid aqueous phase is preferably in the range of 4 to 6, more preferably in the range of 4.5 to 5.5 and even more preferably in the range of 4.7 to 5.3.

The total amount of dissolved tin in the formal oxidation state +II is not critical and may be determined solely by the intended purpose of the liquid aqueous phase and/or the above mentioned solubility of the salt of the stannous ions that is dissolved in the aqueous phase. The total amount of nitrates, which for the purposes of the invention is the total amount of nitrogen measurable as nitrate anions, {N}, is chosen preferably such that there is an excess of nitrates over dissolved tin in the formal oxidation state +II. A typical range for the molar ratio of nitrates to dissolved tin in the formal oxidation state +II is 0.5:1 to 20:1 preferably 5:1 to 15:1.

The inventive combination of dissolved nitrates and non-chelating carboxylic acid is an efficient means for stabilizing liquid aqueous phases containing dissolved tin in the formal oxidation state +II against oxidation by atmospheric oxygen in acidic media.

Dissolved nitrates alone, or in combination with the non-chelating carboxylic acid, may be used in e.g.:

a) Analytical applications wherein the content of dissolved tin in the formal oxidation state +II is to be quantitatively determined by oxidation, whereby a general description of such oxidative assay has already been given above. The stable aqueous stannous ion containing composition comprising a liquid aqueous phase may be the liquid phase of an oral care formulation. Here, it has been observed that the efficacy of the inventive combination in preventing the oxidation of dissolved tin in the formal oxidation state +II is not impaired by the other components found in the liquid phases of oral care formulations. The liquid aqueous phase may also be a mother liquor from a tin-plated scrap metal detinning process. In such detinning process, boiling aqueous sodium or potassium nitrate in alkaline media, with atmospheric oxygen as co-oxidant, is customarily used. The oxidatively dissolved tin should quantitatively be precipitated as stannic oxide or hydroxide, with essentially no dissolved tin in the formal oxidation state +II remaining in the mother liquor. This is a situation where residual trace amounts of dissolved tin in the formal oxidation state +II need to be quantitatively determined; such traces are very prone to be oxidatively degraded during the analysis by the oxidant oxygen and atmospheric oxygen and thus particularly need stabilization. Here, nitrate will normally already be present, and a mineral acid or a non-chelating carboxylic acid may be added to shift the pH to a useful range, to obtain a specimen of a liquid aqueous phase suitable for the analysis.

b) Assays where the efficacy of dissolved tin in the formal oxidation state +II is assayed in various aspects, such as in view of antibacterial activity. Here, during the assay, the dissolved tin in the formal oxidation state +II is again prone to be oxidatively converted to insoluble and thus inactive stannic compounds. The oxidation would give an artificially low efficacy of the dissolved tin in the formal oxidation state +II against the assayed bacterium; the use of the combination of the invention provides stable assaying solutions having a content of dissolved tin in the formal oxidation state +II which is stable over the duration of the assay.

c) Furthermore nitrates, non-chelating carboxylic acid and dissolved tin in the formal oxidation state +II may be preformed in another preferred embodiment into a composition comprising a liquid aqueous phase having a pH of 2 to 4, for use as a storable stock or intermediate solution, which may be added when and as needed as an ingredient in the preparation of oral care formulations. Since such stock or intermediate solution is again stable against oxidation by molecular oxygen it can be stored and handled at a production facility for oral care formulations in tanks or containers for prolonged time without special precautions against oxidation. The oral care formulations that can be prepared by use of such a stock or intermediate solutions can be any type of stannous ion containing oral care formulation customarily comprising an aqueous liquid phase, such as a mouthrinse, a toothpaste, a touching solution or an artificial saliva. The other ingredients or excipients needed to make up such oral care formulations are conventional and can be used without restrictions and in analogy to their use in corresponding oral care formulations. Since this stock or intermediate solution is slightly acidic with pH from 2 to 4, it may directly impart the finished oral care formulation a pH which is physiologically acceptable, i.e. such as from 4 to 6, more preferably from 4 to 5.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

EXAMPLES

Example 1

Analytical Determination of Dissolved Tin in the Formal Oxidation State +II in a Mouthrinse The determination is done by potentiometric iodometric titration using an automatic titrator (Titrando 809 of Metrohm, Switzerland), a platinum electrode (electrode type 6.1204.310 of Metrohm, Switzerland) and a reference electrode. The procedure is illustrative for a target content of up to about 400 ppm dissolved tin in the formal oxidation state +II.

Approximately 50 mL nitrate/acetic acid solution (approximately 2000 ppm nitrates and pH ca. 3 with addition of acetic acid) are transferred into a 150 mL beaker.

Using a volumetric pipette exactly 50.0 mL sample are added.

Under stirring exactly 5.00 mL standard 0.1 N $KI_3$ solution are added to the resulting measuring solution. This is an excess triiodide over the dissolved tin in the formal oxidation state +II.

Remaining triiodide/iodine not reduced by the dissolved tin in the formal oxidation state +II is titrated back just after the addition of the standard $KI_3$ solution with standard 0.1M sodium thiosulfate to the end point. When approaching the endpoint, as visibly by the weakening brownish color of the triiodide, some potato starch may be added, which will become and remain blue as long as any triiodide is present due to its iodine inclusion complex formation.

The content of dissolved tin in the formal oxidation state +II in ppm is calculated as $$\frac{(5.00 - 0.1 \cdot V) \cdot 5.935}{50.0} \cdot 1'000$$

wherein V is the volume of added standard 0.1 M sodium thiosulfate solution at the end point (in mL).

Example 2

Analytical Determination of Dissolved Tin in the Formal Oxidation State +II in Toothpaste The principle, instrumentation and maximum target concentration of dissolved tin in the formal oxidation state +II is as for example 1.

An exactly known amount of toothpaste sample is weighed into a 50 mL beaker. This amount should not be so great such as that the molar amount of dissolved tin in the formal oxidation state +II exceeds 5 mmol. 20.0 mL nitrate/acetic acid solution (see example 1) are added under stirring with a magnetic bar until the sample is completely dissolved and the resulting suspension is homogeneous. The resulting suspension is poured into a disposable 50 mL centrifuge test tube. The beaker is rinsed with additional 10.0 mL nitrate/acetic acid solution and this is added to the test tube. Exactly 10.0 mL diethyl ether are added to the centrifuge test tube, the tube is closed with a solvent tide cap, shaken vigorously for at least 10 seconds and centrifugalized at 4000 rpm for 10 minutes. With a plastic pipette the clear, supernatant ether phase is carefully removed and discarded. The centrifuge vial is closed and shaken vigorously until the suspension is homogeneous again. The resulting suspension is poured in a 150 mL beaker. The centrifuge vial is rinsed with approximately 40 mL nitrate/acetic acid solution and this is added to the beaker. The resulting sample solution is stirred for at least 20 minutes and used in the titration.

The $KI_3$ titration and sodium thiosulfate back-titration is done as in example 1.

The content of dissolved tin in the formal oxidation state +II in ppm is calculated as $$\frac{(5.00 - 0.1 \cdot V) \cdot 5.935}{m} \cdot 1'000$$

wherein V is the volume of added standard 0.1 M sodium thiosulfate solution at the end point (in mL) and m is the above weighed amount of toothpaste sample in g.

Example 3

Measurement of the Content of Nitrates in a Liquid Aqueous Phase

The aqueous phase is firstly filtered to remove any solids, then 1.0000 g±0.1 mg of the filtrate are exactly weighed in a container and water is added to make a total weight of 20.0000 g±0.1 mg.

The determination is done by ion chromatography on a 20 microliter sample of this solution:

Instrument: Dionex IC 25 Ion Chromatograph with autosampler AS 50 with an eluent generator EG 40 with a EluGen Cartridge KOH.

Column: Dionex Ion Pac AS 14, i.d. 4 mm, length 250 mm, with pre-column Ion Pac AG14A, i.d. 4 mm, length 50 mm.

Suppressing system: Dionex Anion Self Regenerating Suppressor, (ASRS-ULTRA II i.d. 4 mm).

Eluent: 40 mM potassium hydroxide solution. This alkaline eluent converts, upon contact with the sample, all nitrates contained therein into nitrate anions.

Flow rate: 0.9 ml per minute.

The molar amount of nitrate anions $\{NO_3^-\}$ in micromoles in the 20 microliter sample is evaluated from the area of the nitrate peak in the ion chromatogram of the sample, using a calibration curve of molar amount of nitrate anions (in micromoles) vs. peak area. This calibration curve is prepared by measuring under the same ion chromatographic conditions 20 microliter aliquots of solutions containing known, but variable molar amounts of potassium nitrate in an useful range.

The numerical value $\{NO_3^-\}$ so obtained, in micromoles, is equal to the molar amount of nitrogen measurable as nitrate ions, $\{N\}$ (in millimoles), in the above 1.0000 g of filtrate. Then, assuming that all types of nitrates dissolved in the aqueous phase contain one $NO_3^-$ moiety each (coordinated or as anion), then said $\{N\}$ is directly equal to the molar amount of nitrates themselves, dissolved in above 1.0000 g of aqueous phase.

Example 4

Comparative Stability Data of Aqueous Solutions of Sodium Nitrate and Stannous Fluoride (Molar Ratio Nitrate: Dissolved Tin in the Formal Oxidation State +II 10:1)

Five aqueous test solutions each containing 267 mg $SnF_2$ and 1.2 g sodium nitrate per 500 mL of solution (nominal content of dissolved tin in the formal oxidation state +II 400 ppm, 0.03 M nitrates) are tested. The test solutions are left in contact with atmospheric oxygen and stirred for 2 days. The actual content of dissolved tin in the formal oxidation state +II is measured at intervals using a procedure similar to the one of example 1.

Further properties of the five test solutions and the observed actual contents of dissolved tin in the formal oxidation state +II (ppm) are according to the following table:

|  | after 5 min | after 3 h | after 30 h |
|---|---|---|---|
| Test solution 1: Non-chelating pH modifier, pH about 7 | | | |
| contains 2.0 g sodium acetate (=0.05M) | 104 | 72 | 34 |
| | | Solution is turbid | |
| Test solution 2: Non-chelating pH modifier, pH about 3 | | | |
| contains 2.0 g sodium acetate (=0.05M) and 25 mL 1M HCl | 380 | 384 | 385 |
| | | Solution is clear | |
| Test solution 3: Chelating pH modifier, pH about 7 | | | |
| contains 11 g sodium gluconate (=0.05M) | 392 | 390 | 372 |
| | | Solution is clear | |
| Test solution 4: Chelating pH modifier, pH about 3 | | | |
| contains 11 g sodium gluconate (= 0.05M) and 25 mL 1M HCl | 372 | 371 | 369 |
| | | Solution is clear | |
| Test solution 5: Without pH modifier, pH about 5 | 403 | 401 | 403 |
| | | Solution is clear | |

Test solution 1 shows that when using a non-chelating deprotonated pH modifier (sodium acetate) and nitrates at neutral pH, the dissolved tin in the formal oxidation state +II is quickly oxidized to stannic ions; a stannic oxide/stannic hydroxide precipitate is formed. Test solution 2 shows that when using a non-chelated protonated pH modifier (acetic acid) and nitrates at acidic pH, the dissolved tin in the formal oxidation state +II slowly starts to re-increase somewhat towards the nominal value after an initial loss during the preparation of the solution. Test solution 3 shows that when using a chelating deprotonated pH modifier (sodium gluconate) and nitrates at neutral pH, there is a slight initial loss of dissolved tin in the formal oxidation state +II which further proceeds over 30 h. Test solution 4 shows that when using a chelating protonated pH modifier (gluconic acid) and nitrates at an acidic pH, there is an initial loss of dissolved tin in the formal oxidation state +II which very slowly proceeds over 30 h. Test solution 5 shows that when using nitrates without additional pH modifier at slightly acidic pH, the dissolved tin in the formal oxidation state +II remains stable against atmospheric oxygen at the nominal content over 30 h.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. A stable aqueous stannous ion containing composition comprising
    a liquid aqueous phase comprising:
        dissolved tin in the formal oxidation state +II,
        dissolved nitrates; and
        a dissolved carboxylic acid which is non-chelating for the dissolved tin in the formal oxidation state +II,
    wherein the liquid aqueous phase has a pH value of 2 to 4.

2. The composition of claim 1, wherein the carboxylic acid is a monocarboxylic acid not substituted by any hydroxy groups.

3. The composition of claim 1, wherein the monocarboxylic acid is selected from the group consisting of C1-C4 linear or branched alkanoic acids, C3-C5 linear, optionally alkyl-substituted alkenoic acids and C6-C14 aryl carboxylic acids.

4. The composition of claim 1, wherein the carboxylic acid is a C1-C4 linear or branched alkanoic acid.

5. The composition of claim 1, wherein the carboxylic acid is acetic acid.

6. A process for improving the stability of tin in the formal oxidation state +II being dissolved in a liquid aqueous phase against oxidation by molecular oxygen, comprising dissolving in the liquid phase a nitrate salt and a carboxylic acid which is non-chelating for tin in the formal oxidation state +II, and adjusting the pH of the liquid aqueous phase to 2 to 4.

7. The process of claim 6, wherein the carboxylic acid is a monocarboxylic acid not substituted by any hydroxy groups.

8. The process of claim 6, wherein the carboxylic acid is selected from the group consisting of C1-C4 linear or branched alkanoic acids, C3-C5 linear, optionally alkyl-substituted alkenoic acids, C6-C14 aryl carboxylic acids and amino acids.

9. The process of claim 6, wherein the carboxylic acid is a C1-C4 linear or branched alkanoic acid.

10. The process of claim 6, wherein the carboxylic acid is acetic acid.

11. A process for the quantitative determination of tin in the formal oxidation state +II being dissolved in an liquid aqueous phase, wherein said tin in the formal oxidation state +II is determined by a quantitative oxidation to stannic ions, wherein the liquid aqueous phase comprises dissolved nitrates.

12. The process of claim 11, wherein the liquid aqueous phase further comprises a dissolved carboxylic acid which is non-chelating for the dissolved tin in the formal oxidation state +II and has a pH value in the range of 2 to 4.

13. The process of claim 11, wherein the carboxylic acid is a monocarboxylic acid not substituted by any hydroxy groups.

14. The process of claim 11, wherein the carboxylic acid is selected from the group consisting of C1-C4 linear or branched alkanoic acids, C3-C5 linear, optionally alkyl-substituted alkenoic acids and C6-C14 aryl carboxylic acids.

15. The process of claim 11, wherein the carboxylic acid is a C1-C4 linear or branched alkanoic acid.

16. The process of claim 11, wherein the carboxylic acid is acetic acid.

17. The process of claim 11, wherein the liquid aqueous phase does not contain any carboxylic acid and has a pH value of 4 to 6.

18. The process of claim 11, wherein the oxidation to stannic ions is done with a pH-independent oxidant.

19. The process of claim 18, wherein the pH-independent oxidant is iodine or triiodide.

20. A process for the preparation of an oral care formulation, comprising mixing the composition of claim 1, and a customary oral care formulation ingredient or excipient.

* * * * *